United States Patent
Wijdenes et al.

(10) Patent No.: US 11,668,698 B2
(45) Date of Patent: Jun. 6, 2023

(54) APPARATUS AND METHOD FOR CAPTURING NEURAL RECORDINGS

(71) Applicant: Neuraura Biotech Inc., Calgary (CA)

(72) Inventors: Pierre Jean Jacques Wijdenes, Calgary (CA); Colin Dalton, Calgary (CA)

(73) Assignee: NEURAURA BIOTECH INC., Calgary (CA)

( * ) Notice: Subject to any disclaimer, the term of this patent is extended or adjusted under 35 U.S.C. 154(b) by 576 days.

(21) Appl. No.: 16/603,092

(22) PCT Filed: Apr. 4, 2018

(86) PCT No.: PCT/CA2018/050411
§ 371 (c)(1),
(2) Date: Oct. 4, 2019

(87) PCT Pub. No.: WO2018/184104
PCT Pub. Date: Oct. 11, 2018

(65) Prior Publication Data
US 2020/0393438 A1    Dec. 17, 2020

Related U.S. Application Data

(60) Provisional application No. 62/481,473, filed on Apr. 4, 2017.

(51) Int. Cl.
*G01N 33/483*    (2006.01)
*G01N 27/00*    (2006.01)
(Continued)

(52) U.S. Cl.
CPC ......... *G01N 33/4836* (2013.01); *A61B 5/685* (2013.01); *G01N 27/00* (2013.01);
(Continued)

(58) Field of Classification Search
CPC .... G01N 33/4836; G01N 27/00; A61B 5/291; A61B 2562/028; A61B 2562/046; A61B 5/685; A61B 2503/42; A61B 2562/0209
See application file for complete search history.

(56) References Cited

U.S. PATENT DOCUMENTS 5,215,088 A    6/1993    Normann et al.
2006/0265039 A1*    11/2006    Bartic ................. A61N 1/0531
607/116

(Continued)

FOREIGN PATENT DOCUMENTS

CN    101006920    8/2007
CN    100431487 C    11/2008
(Continued)

OTHER PUBLICATIONS

EP18781570.9 European Search Report dated Aug. 13, 2020.
(Continued)

*Primary Examiner* — Amy He
(74) *Attorney, Agent, or Firm* — Wilson Sonsini Goodrich & Rosati

(57) ABSTRACT

The present disclosure provides a three-dimensional micro-electrode that comprises an electrically conductive, elongate body with: a base that is electrically connectible to a recording system; a tip that is opposite the base and that is configured to establish electrical communication with an excitable cellular-network or a cell therein; and an elongate portion between the base and the tip. The elongate portion is covered with at least one layer of an electrical-insulator coating that extends from the base to proximal the tip. The present disclosure also provides a micro-electrode array comprising at least two three-dimensional micro-electrodes that are electrically connective to at least one recording system. The present disclosure also provides a method of (Continued)

making and using a three-dimensional micro-electrode and an array that comprises three-dimensional micro-electrodes.

9 Claims, 14 Drawing Sheets

(51) Int. Cl.
*A61B 5/00* (2006.01)
*A61B 5/291* (2021.01)

(52) U.S. Cl.
CPC ......... *A61B 5/291* (2021.01); *A61B 2562/028* (2013.01); *A61B 2562/046* (2013.01)

(56) References Cited

U.S. PATENT DOCUMENTS

| | | | |
|---|---|---|---|
| 2008/0138583 | A1 | 6/2008 | Bhandari et al. |
| 2009/0283425 | A1 | 11/2009 | Clark et al. |
| 2010/0041972 | A1* | 2/2010 | Mason ................ A61B 5/685 607/148 |
| 2013/0105312 | A1 | 5/2013 | Oliver et al. |
| 2019/0021619 | A1* | 1/2019 | Dayeh ................... A61B 5/24 |

FOREIGN PATENT DOCUMENTS

| | | |
|---|---|---|
| CN | 102783942 A | 11/2012 |
| CN | 106054519 | 10/2016 |
| EP | 3607307 A1 | 2/2020 |
| KR | 20140075905 A | 6/2014 |
| WO | WO-2015143443 A1 | 9/2015 |
| WO | WO-2018184104 A1 | 10/2018 |

OTHER PUBLICATIONS

PCT/CA2018/050411 International Search Report and Written Opinion dated Jun. 18, 2018.
Dimaki, Maria, et al., "Fabrication and Characterization of 3D Micro- and Nanoelectrodes for Neuron Recordings", Sensors, vol. 10, 2010, 10339-10355.
Musick, Katherine, et al., "Three-dimensional micro-electrode array for recording dissociated neuronal cultures", Lab Chip., vol. 9, No. 14, 2009, 1-18.
Obien, Marie Engelene J., et al., "Revelaing neuronal function through microelectrode array recordings", Frontiers in Neuroscience, vol. 8, Article 423, 2015, 1-30.
Rajaraman, Swaminathan, "Micromachined Three-Dimensional Electrode Arrays for In-Vitro and In-Vivo Electrogenic Cellular Networks", Georgia Institute of Technology, 2009, 1-268.
Chen, J., The enhancement of a chronically implanted microwire electrode array performance and the investigation of evaluation method. A thesis submitted to Zhengzhou university for the degree of master. Basic Science Series, 2015, No. 2, pp. A006-51.

* cited by examiner

APPARATUS AND METHOD FOR CAPTURING NEURAL RECORDINGS

TECHNICAL FIELD

The present disclosure relates to the field of micro-electrodes. In particular, the present disclosure relates to micro-electrodes and arrays thereof for detecting the electrical activity of an electrically-excitable cell or a network of electrically-excitable cells.

BACKGROUND

The underlying mechanisms of many neurological disorders remain unknown. This lack of knowledge may stem from a limited understanding of neuronal activities, ranging from a single electrically-excitable cell to complex networks of electrically-excitable cells, referred to herein as excitable cellular-networks (ECNs). Understanding the fundamental electrophysiological mechanisms that underlie the formation, maintenance and degeneration of ECNs may assist in resolving the causes and treatments for various neurological disorders.

It is known to study ECNs with planar micro-electrodes that form part of planar micro-electrode arrays (planar-MEAs). The planar-MEAs can interface with an ECN for studying homogeneous neuron populations within controlled extra-cellular environments. It is also known to interface hippocampal brain slices with planar-MEAs to study intact three-dimensional ECNs in an effort to mimic the scenario found in vivo. The preservation of ECNs is crucial when investigating neural function and, in particular, during attempts to perturb the connectivity within the ECN.

However, the signal-to-noise ratio (SNR) within recordings captured by known MEAs, such as planar-MEAs, is often very low and this can interfere with the ability to conduct longer-term experimentation. Longer-term experimentation is desired for various investigations including but not limited to drug screening and in understanding the neural pathways and foci of electrical activity in the brain for various neurological diseases including but not limited to epilepsy. As shown in FIG. 1, the limitations of known MEAs may be due to at least three factors:

1) planar-MEAs 10 only record neural activity from an outer layer 13 of a tissue preparation 12 that includes a network of electrically-excitable cells and the outer layer 13 has a higher population of damaged or dead cells, which are not likely representative of in vivo ECNs, which are found within an inner and undamaged layer 14 of the tissue preparation 12;

2) damaged neurons release different types of ions (mainly potassium), that can be detected by the planar-MEAs 10 and produce a signaling artifact; and 3) the tissue preparation 12 also often require a temperature-controlled perfusion system with a flow of perfusion fluids 16 to provide a continuous flow of nutrients and oxygen, this can create a flow of ions 18 within a gap 20 of the recording chamber and around the electrodes 10 that generates further electrical noise (see FIG. 1).

Overall, recording long-term activity from ECNs is difficult when using planar micro-electrodes or planar-MEAs. Furthermore, the data acquired by using planar-MEAs may be questionable due to the viability of the neurons being recorded, which makes interpretation of that data difficult.

SUMMARY

Embodiments of the present disclosure relate to a three-dimensional (3D) micro-electrode comprising an electrically conductive, elongate body with: a base that is electrically connectible to a recording system; a tip that is opposite the base and that is configured to establish electrical communication with an excitable cellular-network (ECN); and an elongate portion between the base and the tip. The elongate portion is optionally covered with at least one layer of an electrical-insulator coating that extends from the base to proximal the tip. The 3D-microelectrode is configured to come into contact with or penetrate at least partially into a subject's tissue (either in vitro, ex vivo or in vivo) so that the tip is in electrical communication with the one or more cells of the ECN. The electrical-insulator coating may reduce the signal artifact that may arise from passing through the outer layer of the subject's tissue.

Other embodiments of the present disclosure relate to a micro-electrode array (MEA) that comprises at least two 3D micro-electrodes, as described above, which are electrically connectible to at least one recording system. The 3D-MEA can be used to present the tips of multiple 3D micro-electrodes into electrical communication with one or more cells of an ECN. Each 3D-microelectrodes of the 3D-MEA can be selectively fabricated so that all 3D micro-electrodes have substantially the same dimensions of height and diameter or not. Optionally, one or both of the dimensions of height and diameter of each 3D micro-electrode can be selected during the fabrication process so that the 3D-MEA is optimally designed for a given in vitro, ex vivo or in vivo application. For example, 3D micro-electrodes that are positioned within a specific region of the 3D-MEA may be longer to reach further into a specific region of the subject's tissue preparation. Other 3D micro-electrodes that are positioned within a specific region of the 3D-MEA may have a larger diameter in order to establish more robust electrical communication with a specific region of the subject's tissue preparation.

Other embodiments of the present disclosure relate to a method of fabricating 3D micro-electrodes and 3D-MEAs to create a multisite recording platform that permits in vitro, ex vivo and in vivo high-resolution, long-term recording of electrical activity of ECNs with higher signal-to-noise ratio and that cause less tissue damage than known devices. Each 3D micro-electrode that is part of a 3D-MEA can be selectively fabricated so that the dimensions of height and diameter are selected based upon the region of the subject's tissue preparation those 3D micro-electrodes are intended to establish electrical communication with. Optionally, the amount of the tip of each 3D micro-electrode that is bare and not coated in the electrical-insulator coating can be selected as well. Additionally, the shape of the tip of each 3D micro-electrode may also be selectively fabricated between blunt, sharp or flat. The shape of the tip may be selected based upon the region of the subject's tissue preparation that the 3D micro-electrode is intended to establish electrical communication with.

Other embodiments of the present disclosure relate to a method of fabricating a 3D-MEA, the method comprising the steps of: defining two or more electrically conductive pads between a layer of electrical-insulating material upon a substrate. The method includes a step of depositing an electrically conductive material upon the two or more pads to form an elongate portion of a 3D micro-electrode. This step of depositing further comprises one or more steps of: forming a base of the 3D micro-electrode upon each of the two or more pads; selecting a height of the 3D micro-electrode upon the base; and selecting a diameter of the electrically conductive material upon the base.

Known planar micro-electrodes and planar micro-electrode arrays (MEAs) can only record neural activity from the external layer of tissue that contains electrically-excitable cells. In contrast, the selectable length of the 3D micro-electrodes and 3D-MEAs of the present disclosure may allow the 3D micro-electrode tip to access more deeply within the subject's tissue preparation and, therefore, establish electrical communication with undamaged cells. Additionally, the electrically-insulated elongate portions and bases of the 3D micro-electrodes of the present disclosure may decrease the recorded noise from ionic movement within the local environment while providing structural support.

Without being bound by any particular theory, embodiments of the present disclosure may be useful for increasing the understanding and potential treatment of neuro-degenerative diseases such as, but not limited to: Alzheimer, Parkinson and epilepsy. The present disclosure may also be useful for increasing understanding of cognitive, emotional and behavioral abilities within a subject. Embodiments of the present disclosure may also be useful for controlling neuro-prosthetics, providing feedback to the patients and allow for development of personalized medication or therapies for neuro-degenerative diseases. Using embodiments of the present disclosure for research may also be useful for drug screening as well as understanding fundamental brain functions including, but not limited to, neural network phenomena.

BRIEF DESCRIPTION OF THE DRAWINGS

These and other features of the present disclosure will become more apparent in the following detailed description in which reference is made to the appended drawings:

FIG. 1(B) shows a three dimensional micro-electrode array (3D-MEA) according to embodiments of the present disclosure;

FIG. 2 is two schematics of methods of fabricating and using a 3D-MEA according to embodiments of the present disclosure, wherein FIG. 2(A) through (G) shows steps in a fabrication method of a 3D-MEA and FIG. (H) shows a method of using a 3D-MEA;

FIG. 3 is a series of photographs of a 3D-MEA that comprises 3D micro-electrodes according to embodiments of the present disclosure, wherein FIG. 3A is a photograph of the MEA; FIG. 3B is a photograph of a closer view than FIG. 3A of nine 3D micro-electrodes; and FIG. 3C is a scanning electron micrograph image of a tip of one 3D micro-electrode;

FIG. 4 is two photographs of the 3D-MEA of FIG. 3 for use with a tissue preparation that contains an ECN sample, wherein FIG. 4A is a photograph of the 3D-MEA integrated with a recording system; and FIG. 4B is a photograph of the tissue preparation positioned upon the 3D-MEA;

FIG. 12 is two schematics of portions of the 3D-MEA shown in FIG. 10, wherein FIG. 12(A) is a top-plan schematic of an electrode-supporting pad and a wire section; and FIG. 12(B) is a side-elevation view of the pad shown in FIG. 12(A);

FIG. 13 show three sets of example data obtained after implanting an MEA upon a live animal brain, wherein FIG. 13(A) shows an example of electrical communication data obtained using a known electrode; FIG. 13(B) shows an example of electrical communication data obtained using a 3D-MEA according to the present disclosure; and FIG. 13(C) shows evidence of an ictal period within the animal's brain that is followed by a post-ictal period.

DETAILED DESCRIPTION

Definitions

Unless defined otherwise, all technical and scientific terms used herein have the same meaning as commonly understood by one of ordinary skill in the art to which this disclosure belongs.

As used herein, the term "about" refers to an approximately +/−10% variation from a given value. It is to be understood that such a variation is always included in any given value provided herein, whether or not it is specifically referred to.

As used here, the term "electrical communication" refers to a one-way flow of an electrical signal and/or a two-way exchange of electrical signals. The one-way flow of the electrical signal may originate in: at least one electrically-excitable cell, a three-dimensional (3D) micro-electrode according to the present disclosure or both. The two-way exchange of electrical signals refers to both the transmission and receipt of electrical signals by a 3D micro-electrode and at least one electrically-excitable cell. Electrical communication may also refer to the detection and/or transmission of an electrical signal between the 3D micro-electrode and at least one electrically-excitable cell.

As used herein, the term "electrically-excitable cell" refers to a cell that have the potential to communicate charged ions across the cellular membrane in response to an electric, chemical or physical stimuli. In some instances, the electrically-excitable cells can depolarize in a regulated fashion to generate and propagate one or more action potentials or end-plate potentials. Some examples of electrically-excitable cells include but are not limited to all types of neural cells and muscle cells.

As used herein, the term "excitable cellular-network" and the acronym "ECN" refer to a network of electrically-excitable cells that are interconnected so that stimulation of one or more than one electrically-excitable cell within the network will elicit a response in at least one other electrically-excitable cell within the network. The response of at least one other electrically-excitable cell will include a communication of charged ions across its cellular membrane and/or the release of one or more extra-cellular signal molecules.

As used herein, the term "tissue preparation" refers to a subject's tissue that comprises one or more electrically excitable cells and at least a portion of an ECN. A 3D-MEA according to the present disclosure can come into contact with a tissue preparation and establish in vitro, ex vivo or in vivo electrical communication with the one or more electrically excitable cells and at least a portion of the ECN.

Figure 1:
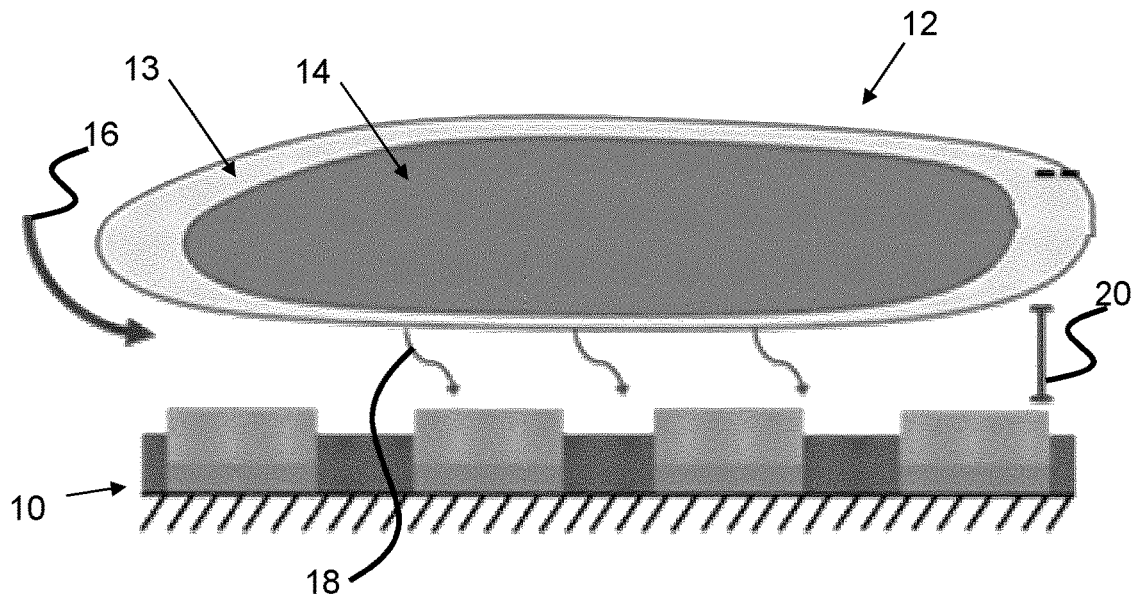
FIG. 1 shows two schematics of micro-electrode arrays, wherein FIG. 1 (A) is a schematic of a tissue preparation positioned upon a prior art planar micro-electrode array (planar-MEA)
Figure 1:
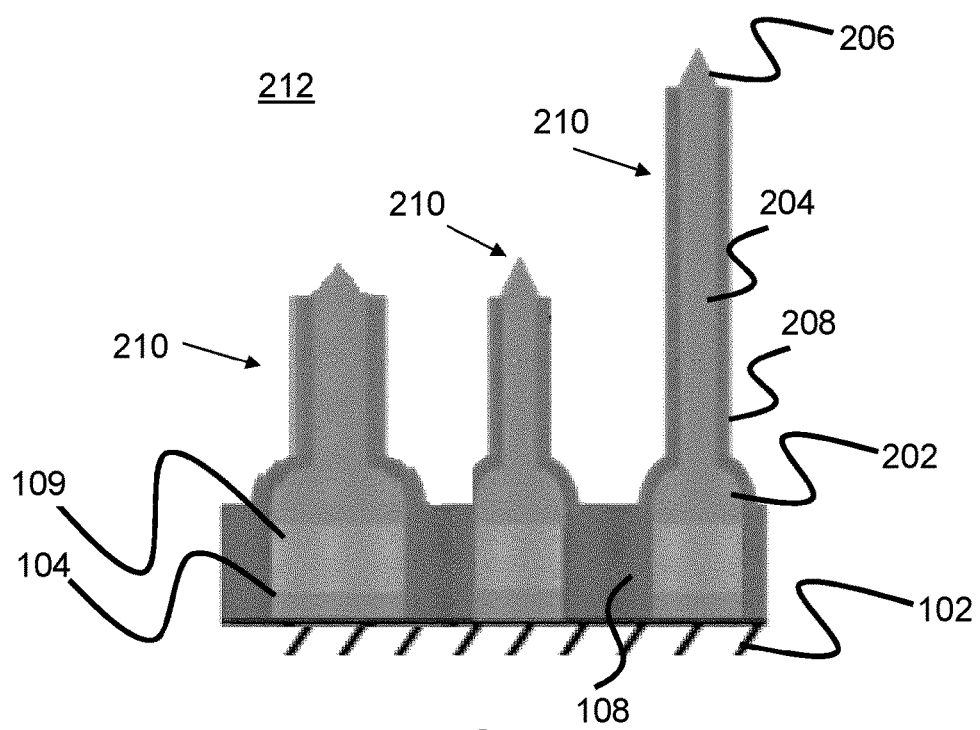

The present disclosure relates to a 3D micro-electrode 210 for establishing electrical communication with a single electrically-excitable cell and/or a network of electrically-excitable cells, which is referred to herein as an excitable cellular-network (ECN) (see FIG. 1(B)). In some embodiments of the present disclosure the 3D micro-electrode 210 comprises an electrically conductive, elongate body 204 with a base 202 that is electrically connectible to a recording system. The 3D micro-electrode 210 also comprises a tip 206 that is opposite the base 202 and that is configured to establish electrical communication with at least a portion of an ECN. The elongate portion 204 is defined between the base 202 and the tip 206. The base 202 typically has a larger diameter than the elongate portion 204 and the elongate portion typically has a greater length than the base 202 and the tip 206. Typically, the tip 206 is frustoconical in shape with a decreasing diameter to a fine point with a diameter that is many times less than the diameter of the elongate portion 204. A substrate 102 can comprise multiple layers (e.g. the additional materials 104 placed in between the substrate 102 and an electrically conductive, electrode supporting pad 109) that support each 3D-microelectrode 210. Some of these multiple layers, or portions of which, may be removed or degraded during the fabrication process. For example the additional material 104 can be placed on the substrate 102 that provides structural support for one or more layers of different materials thereupon (e.g. the layer of conductive material that forms the pads 109). In some instances the substrate 102 is rigid and in some instances the substrate 102 is more flexible. The further layers of materials upon the substrate 102 may be provided to allow different materials (e.g. the different materials that make up the pads 109 and the wires 105) to be attached to the substrate 102.

The elongate portion 204 may be covered with at least one layer of an electrical-insulator coating 208 that extends from the base 202 towards and proximal the tip 206. The tip 206 of the 3D micro-electrode 210 is configured to establish electrical communication with the ECN. The 3D micro-electrode 210 may establish electrical communication with the ECN by direct physical contact, or not. For example, in some embodiments of the present disclosure the 3D micro-electrodes 210 are configured to penetrate at least partially into a tissue preparation 12 (shown in FIG. 2H) that comprises electrically-excitable cells and that make up at least a portion of the ECN.

In some embodiments of the present disclosure at least two 3D micro-electrodes 210 are configured into an array, referred to herein as a 3D micro-electrode array (3D-MEA) 212 (shown in FIG. 1(B)). The 3D-MEA 212 can be used with various types of tissue preparations 12 including, but not limited to: in vitro tissue preparations 12, ex vivo tissue preparations 12 or in vivo tissue preparations 12. In some embodiments of the present disclosure the 3D-MEA 212 can be used to establish electrical communication with the ECN within the tissue preparation 12 for detecting any changes in the electrical activity of the ECN in response to electrical stimuli, chemical stimuli or physical stimuli. In some embodiments of the present disclosure, the 3D-MEA 212 can establish electrical communication for stimulating the ECN within the tissue preparation 12. In some embodiments of the present disclosure, the 3D-MEA 212 can establish electrical communication for both detecting and stimulating the ECN within the tissue preparation 12. The two 3D micro-electrodes 210 of the 3D-MEA 212 are electrically connectible to the same recording system. As shown in FIG. 1(B), an individual 3D-MEA 212 may comprise 3D micro-electrodes 210 that have different lengths and/or different diameters. This is because each individual 3D micro-electrode 210 of a given 3D-MEA 212 can be selectively fabricated based upon the method described herein and the specific dimensions of each 3D micro-electrode 210 can be individually selected based upon the desired application of use of the 3D-MEA 212.

Figure 10:
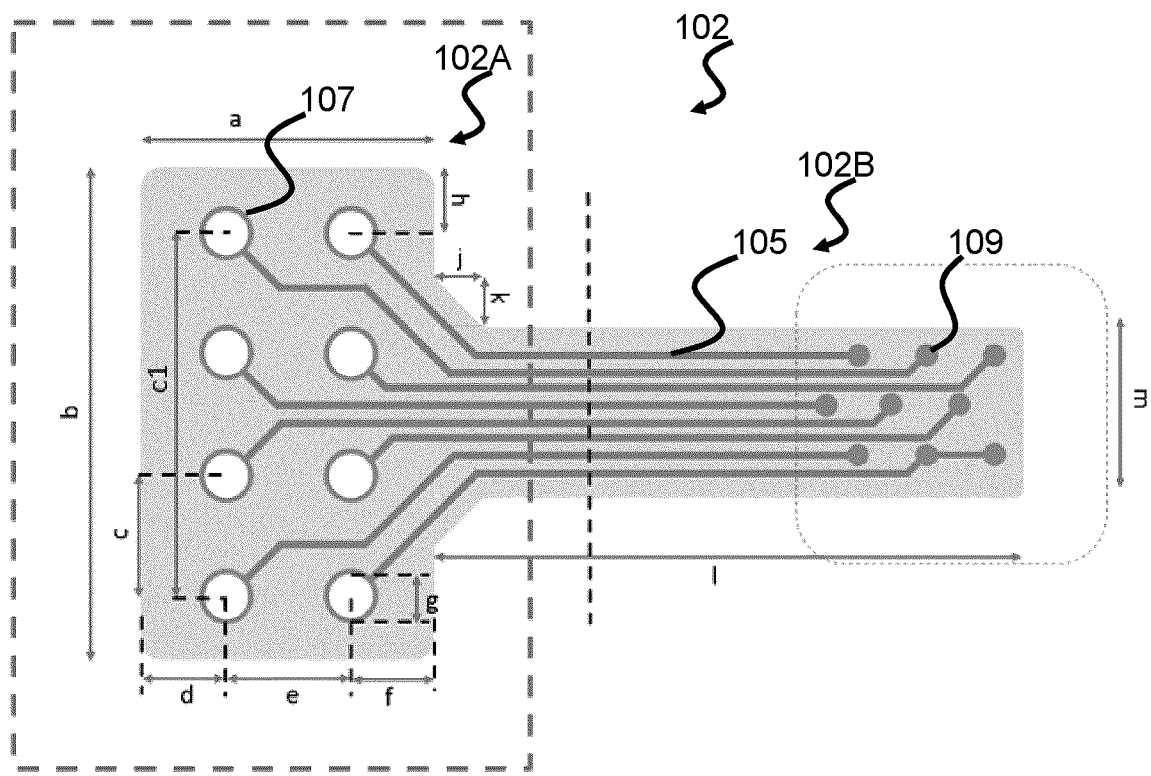
FIG. 10 is a top-plan schematic of a 3D-MEA according to one embodiment of the present disclosure.
Figure 11:
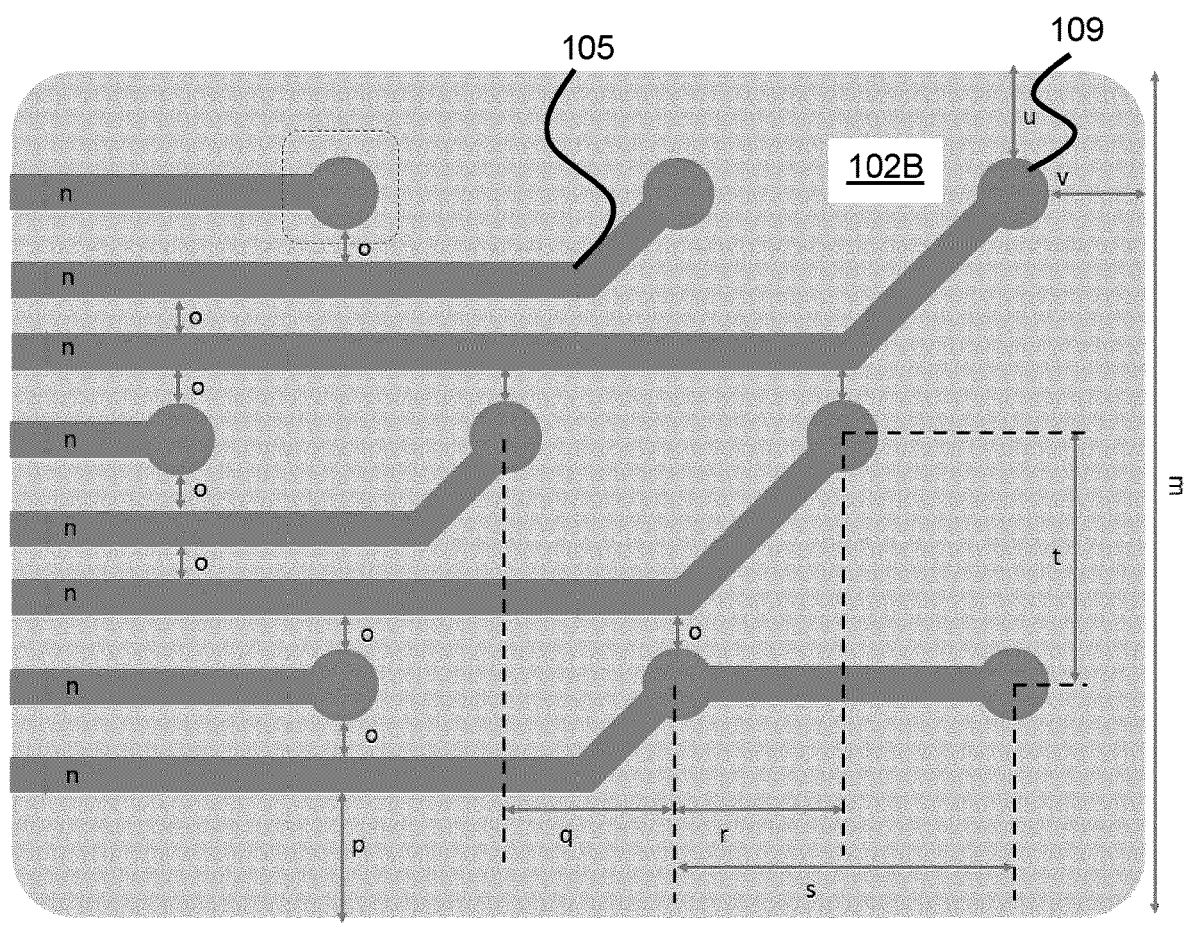
FIG. 11 is a top-plan schematic of one portion of the 3D-MEA shown in FIG. 10.
Figure 12:
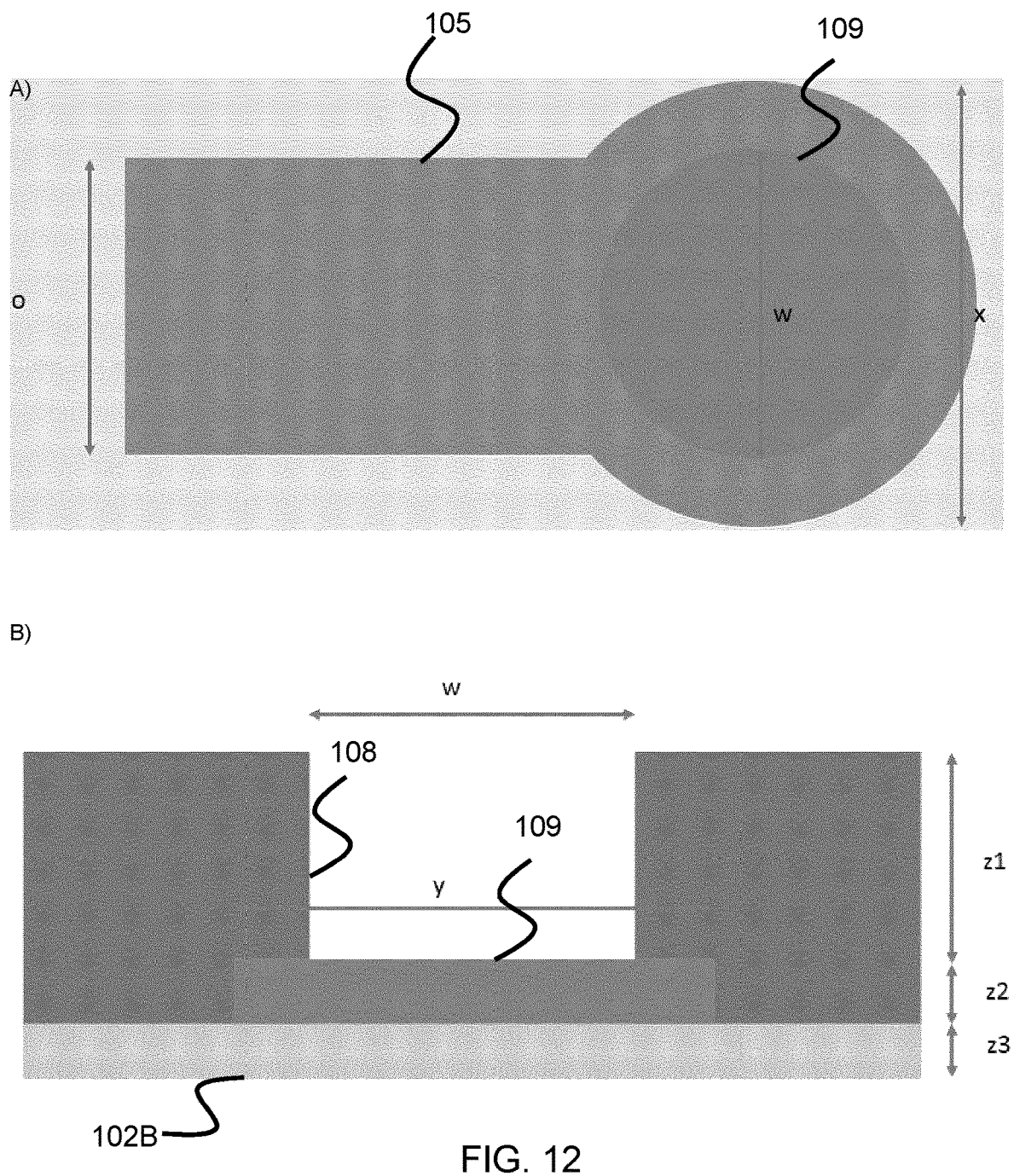

FIG. 10 shows one embodiment of a 3D-MEA 212 that comprises the substrate 102 with a first substrate portion 104A and a second substrate portion 104B. FIG. 10, FIG. 11 and FIG. 12 (A) show planar portions of the 3D-MEA 212. The first substrate portion 104A includes one or more terminals 107 that are configured to provide electronic communication with a transmitter/receiver system (not shown). Extending from each terminal 107 is a wire section 105. The wire section extends from the first portion 104A to the second portion 104B and to the pads 109, which are located in the second portion 104B. The wire sections 105 are electrically conductive and provide electronic communication between each 3D micro-electrode 210 upon a given pad 109 and a given terminal 107. The wire sections 105 can be insulated or not, with one or more insulation layers. Each pad 109 is the location of the 3D-MEA 212 where the base 202 of a 3D micro-electrode 210 is deposited and attached to the substrate 102. In some embodiments, there is a matched relationship between one terminal 107, one wire section 105 and one pad 109. In other embodiments, there may be an unmatched relationship between one terminal 107, one wire section 105 and two or more pads 109. In other embodiments, there may be electronic communication between more than one pad 109 (and the 3D micro-electrode 210 thereupon) and one more than terminal 107.

Figure 14:
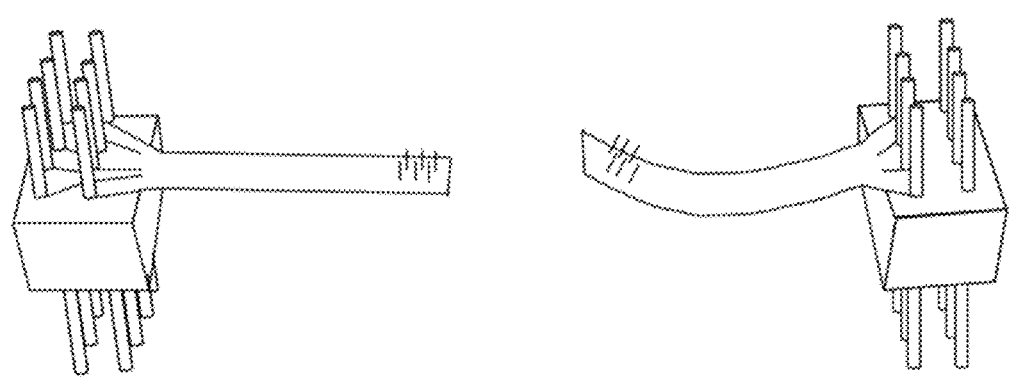
FIG. 14 is a photograph of two flexible 3D-MEAs, according to one embodiment of the present disclosure, wherein one is substantially straight and the other is in a flexed position.

FIG. 14 shows a photograph of two examples of a 3D-MEA 212 with one being in a flexed position between the pads 109 and the first substrate portion 104A.

In some embodiments of the present disclosure, neither portion 104A, 104B is flexible. In some embodiments of the present disclosure, one of or both of the first portion 104A and the second portion 104B are flexible. As will be appreciated by one skilled in the art, having at least one portion of the substrate 102 being flexible is advantageous for establishing optimal physical contact or proximity between the 3D micro-electrodes 210 of a 3D-MEA 212 and the ECN that is defined by an oftentimes, non-flat, flexible surface of the tissue preparation 12.

As shown in FIG. 10, the design of the 3D-MEA 212 can be selected based upon the nature of the tissue preparation 12 that contains the ECN that the 3D-MEA 212 is intended to electrically communicate with. As shown in FIG. 10, the substrate 102 may have a general T shape, or it may take any other desired shape. In the non-limiting example shown in FIG. 10, FIG. 11 and FIG. 12 the first portion 104A and the second portion 104B each define various dimensions that are set out in Table 1 below. The person skilled in the art will appreciate that the dimensions provided in Table 1 are provided as examples only. The dimensions provided in Table 1 were selected based upon the intent of using the 3D-MEA 212 for establishing in vitro electrical communication with a rat brain tissue preparation. However, for other uses with different tissue samples, the 3D-MEA 212 can be selectively fabricated with larger or smaller dimensions than those presented in Table 1 below. For example, a 3D-MEA 212 that is intended to be used with a human subject may be selectively fabricated with larger dimensions than those below in Table 1.

TABLE 1

Examples of dimensions (mm, unless otherwise indicated) of a 3D-MEA according to one embodiment of the present disclosure.

| Letter Indicator | Example Dimension |
| --- | --- |
| a | 0.5 to 10 mm |
| b | 0.5 to 15 mm |
| c | 0.5 to 4 mm |
| c1 | 1.5 to 12 mm |
| d | 0.1 to 2.5 mm |
| e | 0.2 to 5 mm |
| f | 0.1 to 2.5 mm |
| g | 0.1 to 1 mm |
| h | 0.1 to 3.5 mm |
| j | 0.1 to 3 mm |
| K | 0.1 to 3 mm |
| L | 0.5 to 15 mm |
| M | 0.5 to 15 mm |
| N | 0.05 to 1.5 mm |
| o | 0.05 to 1.5 mm |
| p | 0.05 to 2 mm |
| q | 0.01 to 5 mm |
| r | 0.01 to 5 mm |
| s | 0.05 to 5 mm |
| t | 0.05 to 5 mm |
| u | 0.02 to 2 mm |
| v | 0.02 to 2 mm |
| w | 0.01 to 1 mm |
| x | 0.01 to 1 mm |
| y | 0.01 to 1 mm |
| z1 | 0.005 to 25 µm |
| z2 | 200 nm to 15 µm |
| z3 | 0.001 to 1 mm |

In the embodiments of the 3D-MEA 212 that can be used with in vivo ECNs, the 3D-MEA 212 can be manufactured on to a flexible and biocompatible substrate 102 that is configured to be implanted into a living organism. The 3D-MEA 212 can also be configured to detect the electrical activity of the in vivo ECN and/or to stimulate the in vivo ECN or specific regions thereof.

Some embodiments of the present disclosure relate to a fabrication method of making a 3D micro-electrode 210 and a method of making a 3D-MEA 212. The 3D micro-electrodes 210, either as an individual 3D micro-electrode 210 or as part of a 3D-MEA 212, can be made individually with precise control of: the height and diameter of each 3D micro-electrode 210 within the 3D-MEA 212; the length of the elongate portion 204 that is covered in the electrical-insulator material 208; the length of the tip 206; and the shape of the tip 206. The spacing and positioning of each 3D micro-electrode 210 within the 3D-MEA 212 and upon the substrate 102. The fabrication method allows the selectability of the materials used to make the 3D micro-electrodes 210, the electrical insulating coatings 208 and the materials of each layer of the substrate 102 upon which the 3D-MEA 212 is built. The fabrication method also allows for selectability of the surface area of each 3D micro-electrode 210 that is not covered by the electrical insulating coating 208 and the position of these uncovered sections within the 3D-MEA 212.

Figure 2:
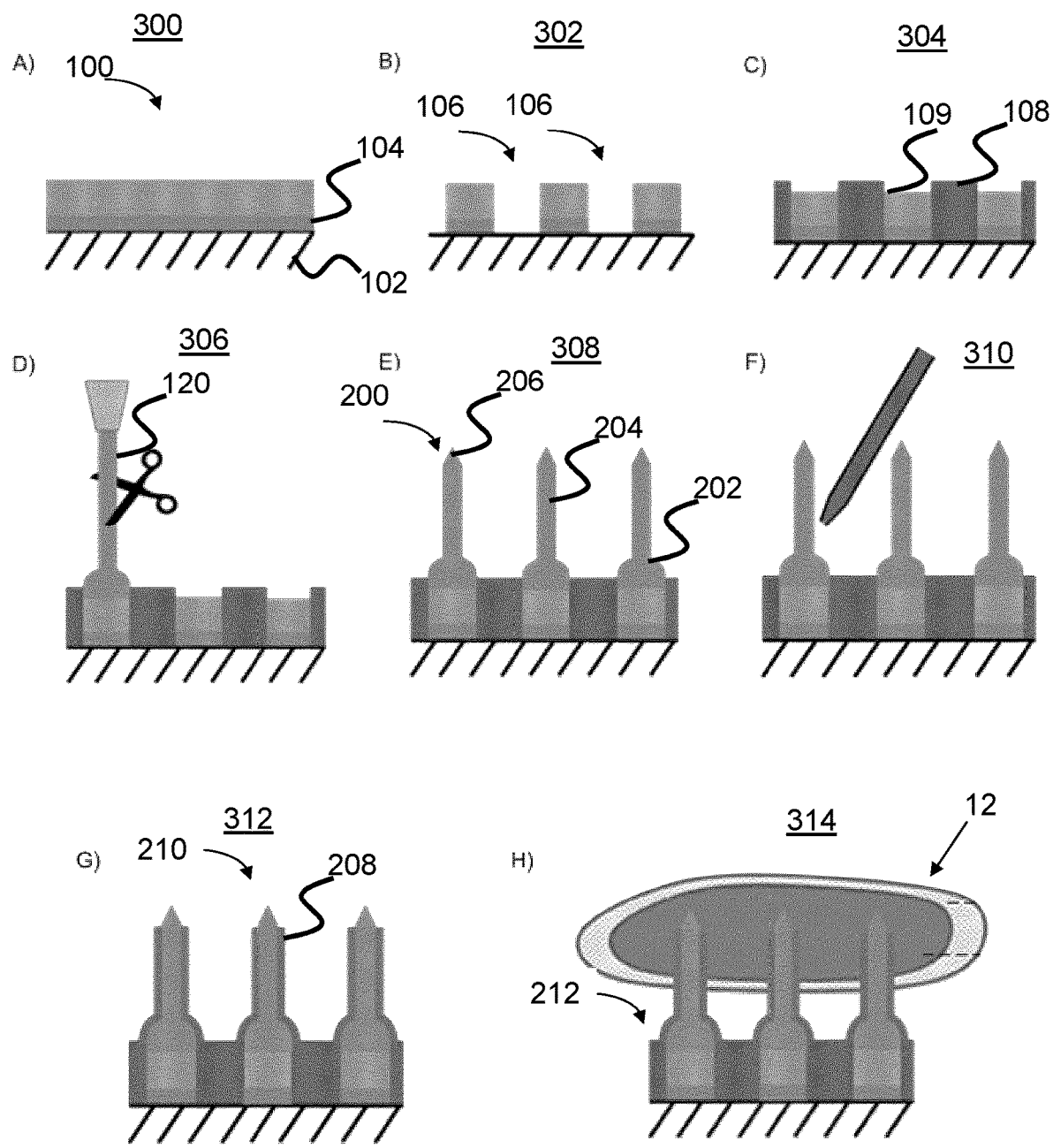

As shown in FIG. 2, the fabrication method comprises a step to establish 300 a first layer comprised of one or more materials 104 and conductive materials that form the electrically conductive, electrode supporting pads 109 upon the substrate 102. The product of this first step is referred to as a coated blank 100. The next step of the fabrication method is to establish 302 one or more grooves 106 upon the coated blank 100 by removing one or more layers of the substrate 102. The next step of the fabrication step is to position 304 an electrical-insulating material 108 between the grooves to define one or more pads 109. Alternatively, the electrical-insulating material 108 can be deposited upon the substrate 102 and then substantially removed from the location of the pads 109. Alternatively, a layer of the electrical-insulating material 108 can have holes defined therein, and then that insulating layer can be adhered to the substrate 102 with pads 109 already thereupon. The holes in the insulating layer will align with the pads 109. As shown in FIG. 12B, optionally the electrical-insulator material 108 can cover, or overlap, the peripheral edges of the pad 109. This overlap provides some additional rigid support while depositing the 3D micro-electrode 210 upon the pad 109.

The next step in the fabrication method is to deposit 306 a conductive material upon the one or more pads 109. The step of depositing 306 can occur by various methods, including but not limited to: wire bonding, sputtering, electrodeposition, evaporation, extrusion, combinations thereof or other methods to make a conductive material of a desired geometry. The step of depositing 306 may further include a step of selecting the diameter of the elongate portion 204 of the 3D micro-electrode 210. For example, if a particular 3D micro-electrode 210 was intended to penetrate deeper into a portion of the tissue preparation 12, then that 3D micro-electrode 210 may have a smaller diameter so that it is less invasive as it moves through the tissue preparation 12. In some embodiments of the present disclosure the diameter of each elongate portion 204 may be selected within a range of between about 1 microns and 1000 microns. In some embodiments of the present disclosure, the diameter of the elongate portion 204 may be selected to be within a range of between about 5 microns and about 750 microns. In some embodiments of the present disclosure, the diameter of the elongate portion 204 is between about 5 and 1000 microns.

The step of depositing 306 includes forming the base 202 and a step of selecting the height of the 3D micro-electrode 210. The selecting of the length can include a step of stopping the depositing 306 of the conductive material upon the pad 109 and/or cutting the conductive material as it is being deposited. In some embodiments of the present disclosure, the length of the 3D micro-electrode 210 is selected by cutting the conductive material. Some of the methods of cutting the conductive material include, but are not limited to: using micro-scissors, electronic flame off (EFO)—whereby the conductive material is heated at a very localized position such that it melts and cuts the conductive material, use of a laser to cut the wire at a selected height, physically pulling the wire until it stretches and then breaks due to mechanical stresses, or combinations thereof. In some embodiments of the present disclosure the length of each elongate portion 204 may be selected within a range of between about 1 micron and 10 cm. In some embodiments of the present disclosure the length of each elongate portion 204 may be selected within a range of between about 1 micron and 5 cm. In some embodiments of the present disclosure, the length of the elongate portion 204 may be selected to be within a range of between about 5 microns and about 1000 microns. In some embodiments of the present disclosure, the length of the elongate portion 204 is between about 25 and 500 microns.

When the 3D micro-electrode 210 is formed with the selected length, the end of 3D micro-electrode 210 that is opposite to the base 202 is referred to as the tip 206. The elongate portion 204 of the 3D micro-electrode 210 is defined between the base 202 and the tip 206. The tip 206 is the portion of the elongate portion 204 that is not coated with the electrical-insulating coating 108. Furthermore, the method of selecting the height of the 3D micro-electrode 210 may also include providing the tip 206 with either a sharp, a blunt or a flat shape.

In order to make multiple 3D micro-electrodes 210 of an MEA 212, the steps 302 to 306 can be repeated 308 to selectably fabricate the desired number of electrodes 210 in multiple locations on the substrate with the same or different diameters and lengths. When one or all of the desired electrodes 210 are fabricated, the next step is to coat 310 the electrodes 210 with the electrical-insulating coating 108. In addition having dielectric properties, the insulating materials may have other desirable properties such as, but not limited to, being curable, photoresistant, waterproof, biocompatible or combinations thereof. Some examples of suitable materials for the electrical-insulating coating 108 includes, but is not limited to, dielectric and insulator materials, such as photoresists (both positive and negative), polymers, oxides, nitrides and ceramics. In the present case, the material SU8 was utilized. SU8 is a chemically amplified, epoxy based negative photoresist that is optically transparent and photo-imageable to near ultraviolet (UV) (about 365 nm) radiation. Cured films or microstructures of SU8 are very resistant to solvents, acids and bases, have excellent thermal and mechanical stability and are biocompatible when cured. The coating step 310 can be achieved by various methods including, but not limited to: sputtering, spin coating, evaporation, casting, pouring, syringe dispensation, micropipette dispensation, combinations thereof or other methods that are commonly known to one skilled in the art. The fabrication method also includes a step of selecting 312 how much surface area and/or which portion(s) of the 3D micro-electrode 210 are coated with the insulating material. As shown in FIG. 2(G) the step of selecting can result in some, most or all of the elongate portion 204 being coated in the insulating material. In some embodiments of the present disclosure, some, most, all or none of the tip 206 is coated in the insulating material. In some preferred embodiments, none of the tip 206 is coated in the insulating material.

Some embodiments of the present disclosure relate to a detection method for detecting the electrical activity of an ECN. The detection method may comprise a step 314 of positioning the tips 206 of each 3D micro-electrode 210 within a tissue preparation 12 that comprises at least a portion of an ECN. For clarity, the tissue preparation 12 may be an in vitro preparation, an ex vivo preparation or an in vivo preparation. The step 314 positioning includes positioning the 3D-MEA 212 proximal to an ECN and then establishing electrical communication between one or more 3D micro-electrodes 210 of the 3D-MEA 212 and the ECN. The step of establishing electrical communication may include receiving (also referred to as detecting) electrical signals from the ECN and/or transmitting electrical signals from the 3D-MEA 212 to the ECN. The detection method may further comprise a step of stimulating the ECN and detecting any changes in the electrical activity of the ECN. The ECN can be stimulated electrically (via the 3D-MEA 212 or not), mechanically or chemically.

The electrical communication is transmitted from each electrode to a transmitter/receiver system (not shown). The transmitter/receiver system may transmit an output signal from each 3D micro-electrode 210 to a processor (not shown) for example when the 3D-MEA 212 is receiving electrical signals from the ECN. The transmitter may also transmit a processor signal to each 3D micro-electrode 210, which each electrode transmits to the ECN.

EXAMPLES

Example 1

3D-MEA Fabrication

Planar electrodes in 8×8 array configuration were fabricated using photolithography onto a substrate that had a rigid glass, base substrate layer and that measured 49 mm×49 mm×1 mm. The substrate included a 50 nm chrome adhesion layer that was coated by sputter deposition and the adhesion layer was then coated with about 400 nm of gold (FIG. 2A). The size, shape and the spacing between the planar micro-electrodes can be adjusted according to experimental needs using different photomasks during the photolithography process. In the present examples, the planar micro-electrodes were fabricated with a diameter of about 100 µm and with inter-electrode spacing of about 500 µm (FIG. 2B). A first electrical-insulator layer was formed with an epoxy photoresistant material (SU8), which was spin coated over the entire 3D-MEA. The insulator layer was then patterned with a second photomask to leave the planar electrodes bare of SU8 insulator, but with their connecting wires insulated (FIG. 2C). This formed the pads of the 3D-MEA.

3D micro-electrodes with a base, an opposite tapered tip and an elongate portion therebetween were added onto the pads of the planar electrodes using a manually programmable wire bonder (West-Bond model 454647E). Briefly, the 3D micro-electrodes were created by bonding gold wires onto the planar electrodes at the base of the 3D micro-electrode, manually extending the gold to a predetermined height and then cutting the gold wires with micro-scissors mounted on micro-manipulators (FIG. 2D and FIG. 2E). This cutting step formed a tip of the 3D micro-electrode that can be tapered, beveled, blunt or substantially flat. This method yields control and flexibility in the diameter and the height of each 3D micro-electrode and the inter-electrode spacing. Electrically conductive materials other than gold may also suitable for making the 3D micro-electrodes including but not limited to: aluminum, aluminum alloys such as. 0.5-1% magnesium-aluminum or silicon-aluminum, carbon, iridium, indium, titanium, copper, silver, palladium, platinum and combinations thereof and any other material that can be used in or adapted for any process to create 3D micro-electrodes, including at least a wire-bond process. The micro-electrodes can also be individually fabricated and addressable. For example, the 3D gold micro-electrodes were fabricated with controlled heights ranging from about 50 microns (µm) to about 400 µm with a diameter of between about 8 µm to about 500 µm depending on the bonder wires used. However, smaller or larger heights and diameters of 3D micro-electrodes are also contemplated by the present disclosure. These heights, spacing and materials were chosen specifically for recording from a 400 µm thick murine brain-slice but the 3D micro-electrode height and diameter and the 3D-MEA inter-electrode spacing may be adjusted individually, either increased or decreased, to suit other types of ECNs or different experimental arrangements with similar or different ECNs.

Figure 3:
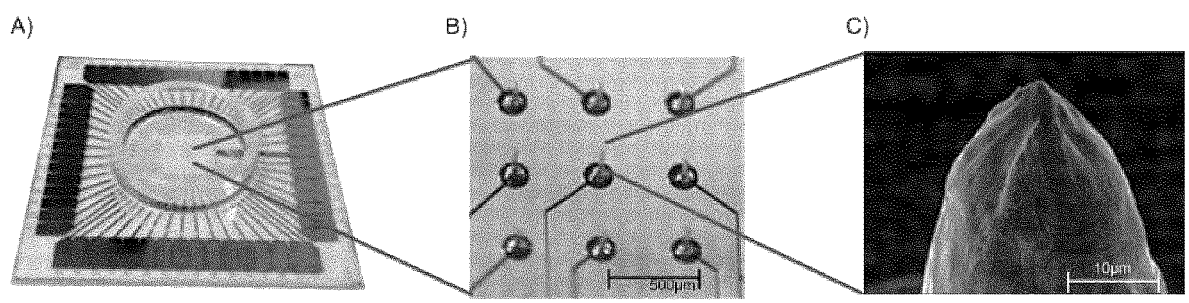

A second electrical-insulator layer may be made up of the epoxy photoresist SU8 that was locally deposited on the bases and edges of the newly formed 3D micro-electrodes using a fine sharp glass micropipette with a 30 µm tip opening whose positioning was accurately controlled using a 3-axis micromanipulator (FIG. 2F and FIG. 2G). This micropipette was connected through a plastic tube to a syringe containing the SU8, which was itself mounted on a syringe micro-pump to control the flow (Harvard Apparatus Co., Dover, Mass., USA, Dual infusion/withdrawal pump model 942). The SU8 was then cured with UV light to form the second electrical-insulator layer upon the 3D micro-electrodes. This process allowed the 3D-micro-electrode tips to be left without any of the second electrical-insulator layer for the last few micrometers so that the tip could establish electrical communication by direct contact with the healthy neural cells inside the brain slice (FIG. 2). The amount of surface area of the tip that can come into direct contact with the neural cells can be adjusted by adding more or less of the second electrical-insulator layer on the 3D micro-electrodes of the 3D-MEA. A glass ring was then placed on the 3D-MEA to form a recording chamber (FIG. 3A).

Example 2

ECN Sample Preparation

Figure 4:
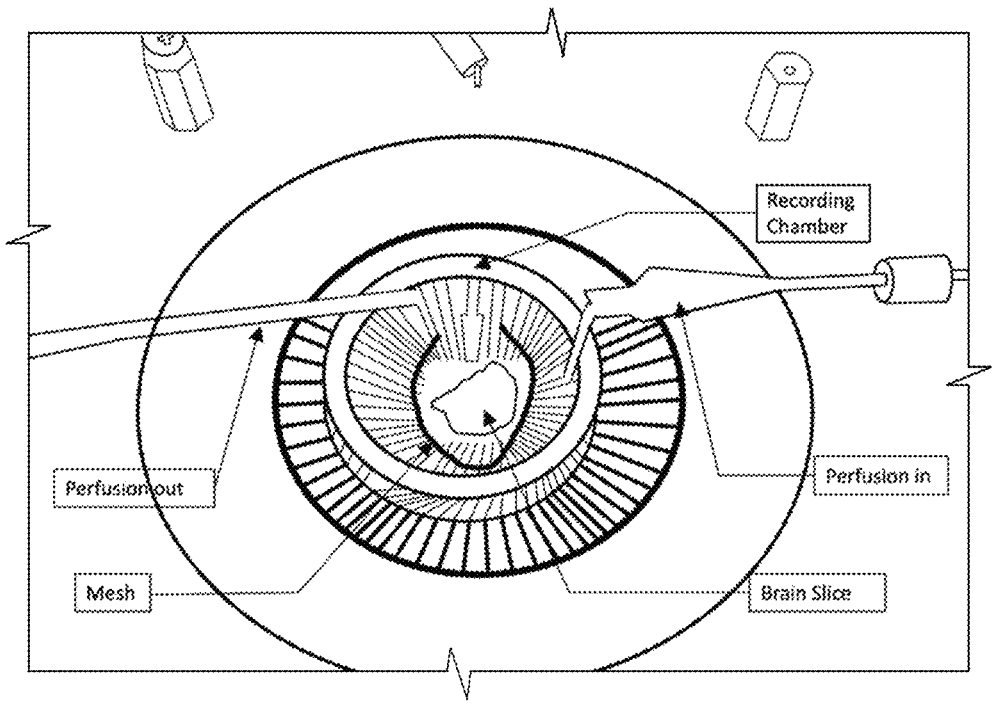
Figure 4:
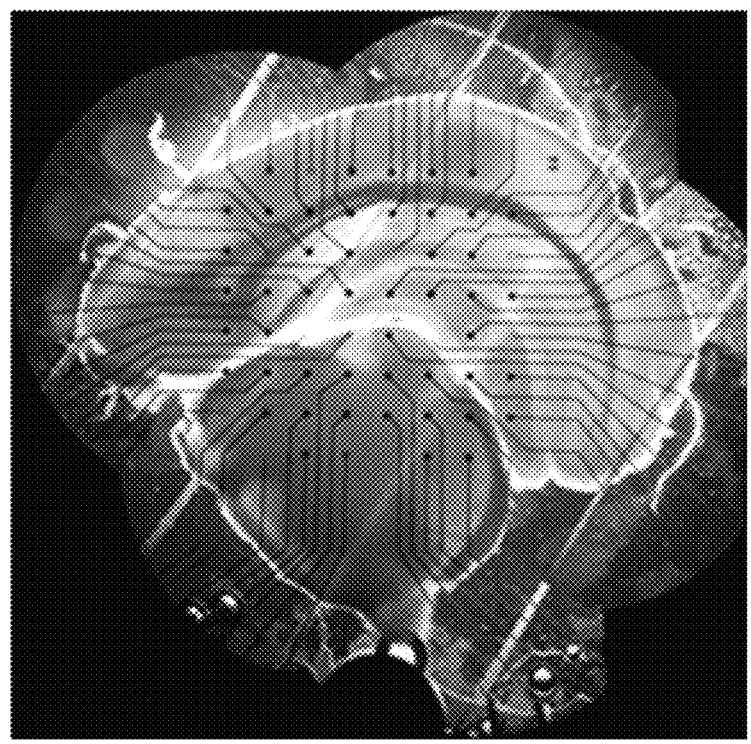

After cleaning and sterilizing the 3D-MEA, poly-L-lysine was used as a coating to enhance the interfacing between the electrodes and the neural cells. As a sample of an ECN, acute hippocampal brain slices from wild-type mice littermates (P35) were positioned in the recording chamber, with the help of an optical microscope, and anchored onto the 3D-MEA by means of a mesh to prevent movement and to facilitate the penetration of the 3D micro-electrodes into the ECN sample (FIG. 4). In FIG. 4 (and FIG. 7) the small dark circles are the bases the 3D micro-electrodes, and the dark lines extending therefrom are the electrodes traces that connect each 3D micro-electrodes to the recording system on the outside of the 49 mm×49 mm glass substrate.

Figure 5:
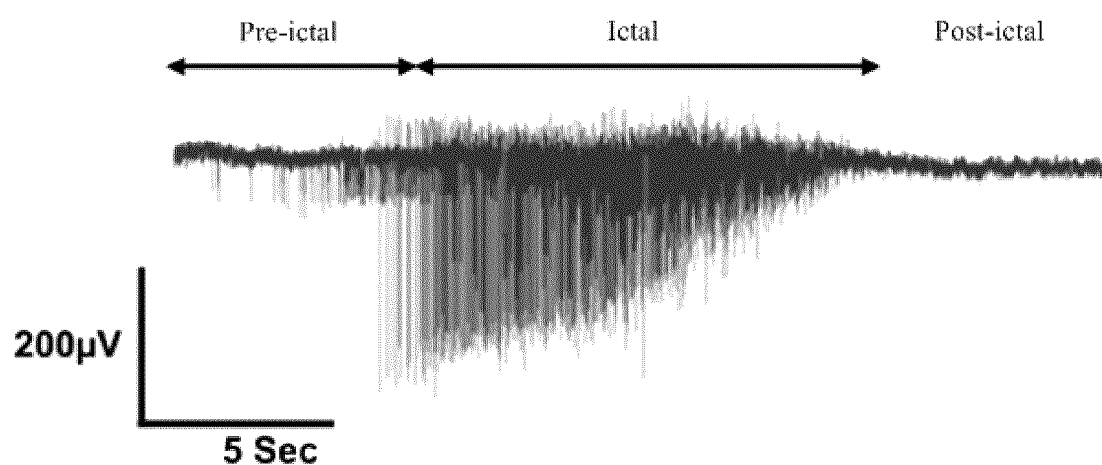
FIG. 5 shows an example of a recording of electrical activity detected from an ECN sample using the 3D-MEA of FIG. 3.
Figure 6:
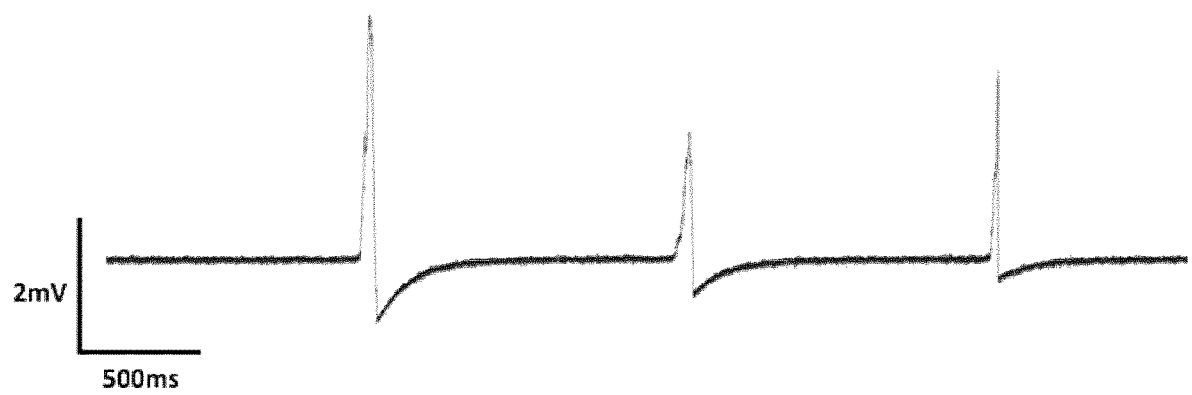
FIG. 6 shows another example of a recording of electrical activity detected from an ECN sample using the 3D-MEA of FIG. 3.

To demonstrate the capabilities of the 3D-MEA to detect electrical activity within distinctive environments that stimulate spontaneous neural activity at the ECN level, the recording chamber was perfused with either one of three types of artificial cerebrospinal fluid (aCSF): (1) "normal" aCSF; (2) "low" aCSF with 0 mM of $Mg^{2+}$; and (3) "high" aCSF with 8.5 mM of $K^+$. All of the aCSF were used at about 32° C., with about 5% $CO_2$ and about 95% $O_2$. The different ion concentrations in the aCSF types (2) "low" and (3) "high" can cause spontaneous neural-activity to occur within the murine brain slices and are known to induce spontaneous seizure-like activity within murine brain slices. Spontaneous, seizure-like activity is referred to herein as an ictal phase. A recording system (MEA1060; Multichannel Systems, Reutlingen, Germany) was then electrically connected with each 3D micro-electrode of the 3D-MEA to collect data at a 10 kHz sampling rate (FIG. 5 and FIG. 6).

After positioning the hippocampal brain slice over the 3D-MEA while being perfused with an "activity triggering" aCSF (either the type (2) "low" or type (3) "high"), spontaneous neural activity was consistently recorded (n=50+, 98% of the time) in vitro at multiple 3D micro-electrodes within the 3D-MEA and across the different channels. The recorded neural activity could be tracked within the entire brain slice and specific pathways could be identified. This activity would consist of bursting pre-ictal and ictal events, localized or not, high frequency activity (greater than 80 Hz) as is often seen in mammalian brains that are undergoing seizures (FIG. 5).

Without being bound by any particular theory, the 3D micro-electrodes and the 3D-MEAs of the present disclosure may offer opportunities to track high frequency bursting activity between different areas of a brain slice and analyze its overall excitability.

Example 3

Signal-to-Noise Ratio (SNR)

The SNR of the 3D micro-electrodes was then compared with earlier reported devices, including other three-dimensional (e.g. pyramidal-shaped) and planar micro-electrodes. The 3D micro-electrodes of the present disclosure demonstrated an average noise reduction to about 20 µV as compared to about 40 µV to about 60 µV observed in traditional planar micro-electrodes. Also, the 3D micro-electrodes provided a highest recorded field potential activity peak-to-peak, which was in the mV range (about 3.2 mV) as compared with recordings of <1 mV that were captured with traditional planar micro-electrodes (FIG. 6). Overall, the 3D micro-electrodes and the 3D-MEAs of the present disclosure may offer a higher signal-to-noise ratio (with a greater than 300% improvement) than commercially available devices using traditional planar micro-electrodes.

Because these 3D micro-electrodes record activity from within brain slices, where the healthy cells remain, and because the electrical-insulator layer is present on the base and the micro-electrodes elongated section (but not the tip), continuous long-term electrical activity was recorded. A temporal resolution may refer to either the time length of a given recording or the frequency of the recording, i.e. how many data points are recorded per second. In the present disclosure, the maximum time length of recording was about 3 hours and frequency of the recording can go up to about 50 kHz. It is also worth highlighting that the cured SU8 (the electrical-insulator layer) on the electrodes' edges provides structural support and reduces the physical degradation of the three-dimensional electrodes, thus allowing the MEAs to be re-used multiple times.

Figure 7:
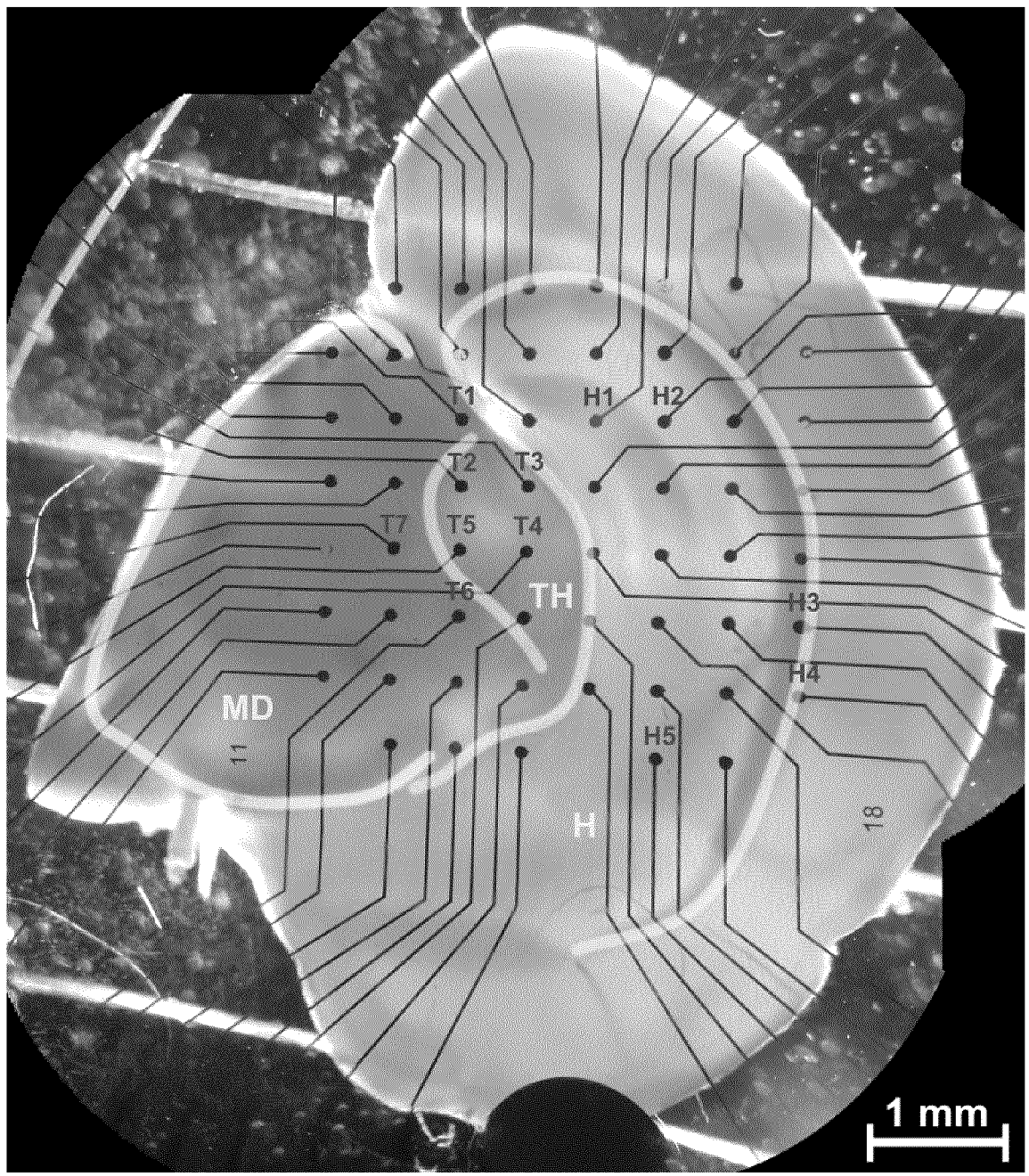
FIG. 7 shows a picture taken with an optical microscope of an acute hippocampal brain slice positioned on an array of electrodes. Areas such as the mid-brain (MD), the thalamus (TH) with sub-areas T1, T2, T3, T4, T5, T6 and T7 identified and the hippocampus (H) with sub-areas H1, H2, H3, H4 and H5 identified.
Figure 8:
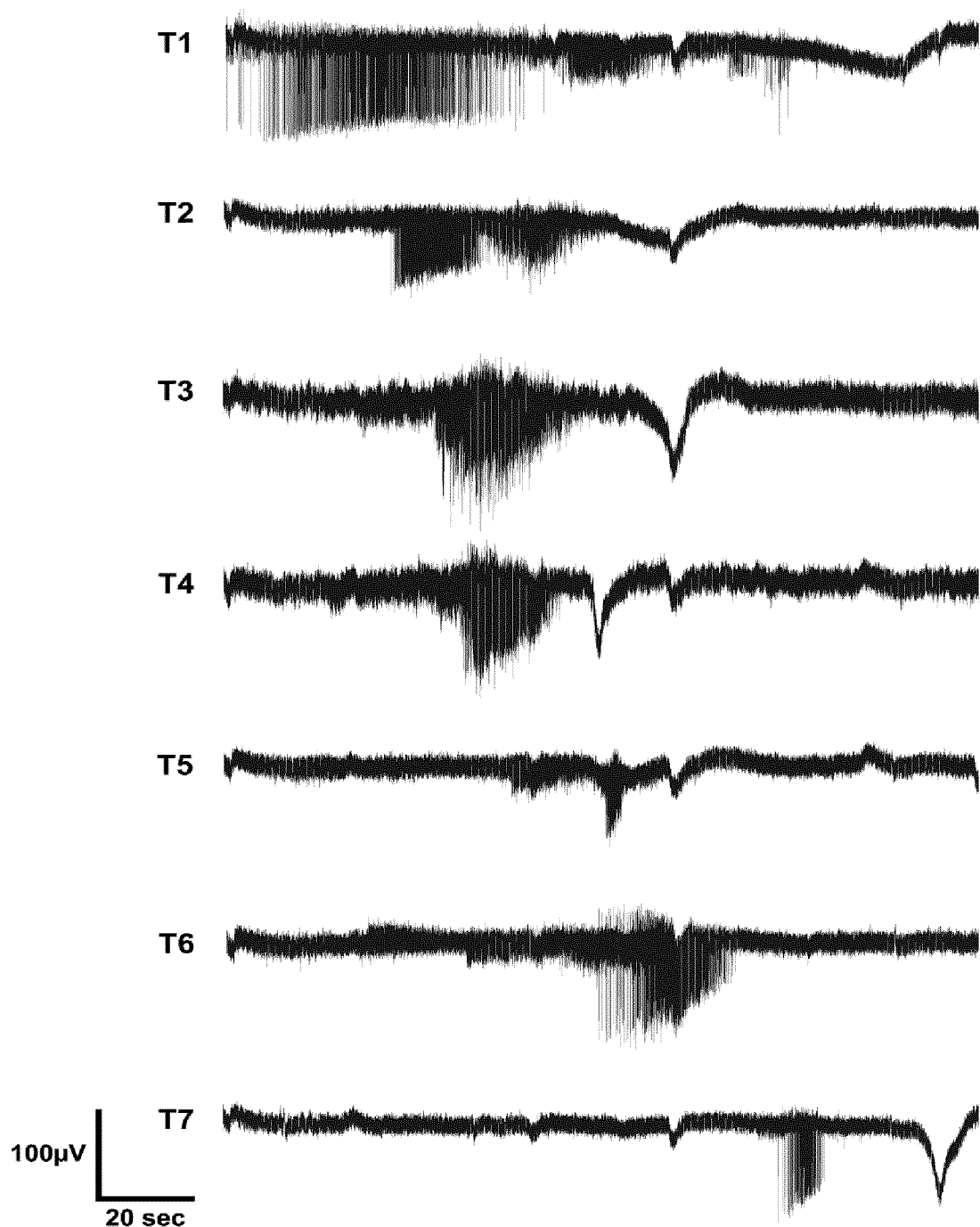
FIG. 8 shows examples of electrical activity recorded within the thalamus sub-areas T1 through T7.
Figure 9:
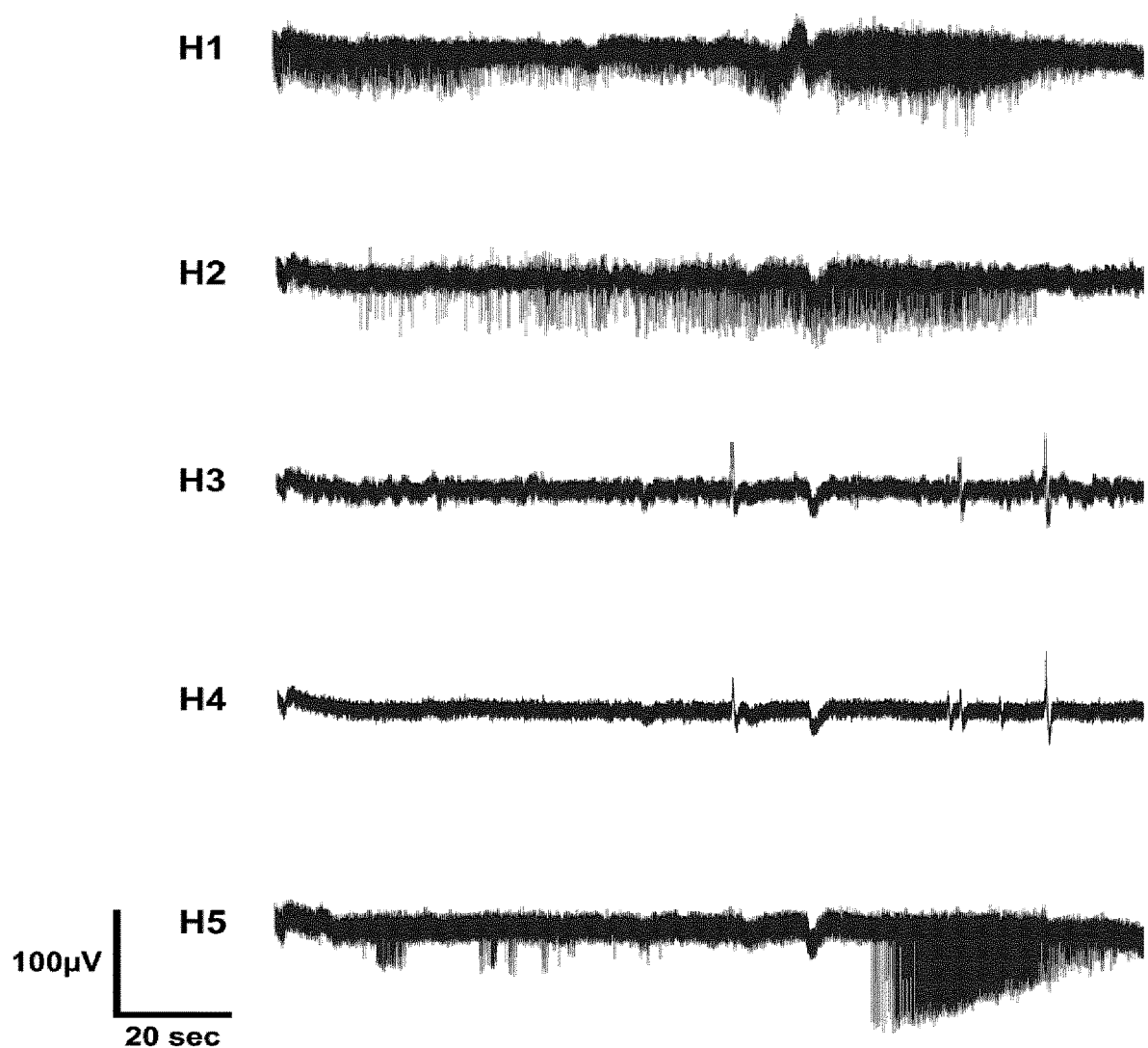
FIG. 9 shows examples of electrical activity recorded within the hippocampus sub-areas H1 through H5.

FIG. 7 shows a picture taken with an optical microscope of an acute hippocampal brain slice positioned on an array of electrodes. Areas such as the mid-brain (MD), thalamus (TH) and hippocampus (H) are clearly visible. FIG. 8 shows the spontaneous electrical activity that was recorded using an embodiment of the present disclosure from sub-areas of the TH, including T1 to T7, whose positions are indicated on FIG. 7. FIG. 9 shows the spontaneous electrical activity that was recorded using an embodiment of the present disclosure from sub-areas of the H, including H1 to H5, whose positioned are indicated on FIG. 7.

Example 4

Manufacturing an In-Vivo MEA

A similar method to the one described above for fabricating the in-vitro 3D-MEA was used to manufacture an implantable, and optionally flexible, 3D-MEA that can record activity from electrically excitable cells in vivo. For example, the primary difference between the fabrication method described herein above for making the in vitro 3D-MEA and the in vivo 3D-MEA of the present example is that the planar electrodes were fabricated on a flexible substrate. The method steps for making the 3D micro-electrodes includes the same steps as described above.

Various materials can be used for the substrate, the wires, the electrodes, and the electrical-insulator layer. The patterning of the wires and the electrodes can be performed in multiple ways. To record electrophysiological activity from electrically excitable cells, low impedance and high conductivity materials are preferred for making the wires and the electrodes. In the present example, a flexible printed circuit board (flex PCB) was used as the substrate. The wires were made of copper using copper electrode traces subsequently coated by an Electroless Nickel Immersion Gold (ENIG) process to create wires and biocompatible electrode pads upon the flex PCB. The 3D micro-electrodes were then fabricated on top of the electrode pads and their bases and edges were insulated by coating with the electrical-insulating material that is biocompatible. One non-limiting example of such an insulating material is SU8, but other insulating and biocompatible materials are known to those skilled in the art. Optionally, the materials for fabricating the electrodes were selected from low impedance, high conductivity and magnetic resonance imaging (MRI) benign materials, for example gold, platinum and other known materials.

Referring to FIG. 10, which shows a top plan view of a schematic of one example of the in vivo 3D-MEA without the 3D micro-electrodes manufactured upon the pads 109. The in vivo 3D-MEA had the following dimensions, which are provided as an example only and not as a limitation upon the embodiments of the present disclosure: a—3 mm, b—5.04 mm, c—1.27 mm, c1—3.81 mm, d and f—0.865 mm, e—1.27 mm, g—0.5 mm, h—0.651 mm, j and k—0.5 mm, l—8 mm, m—1.75 mm, n and o—75 micron, q and r—350 micron, s—700 micron, t—525 micron, u and v—200 micron, w—100 micron, x—150 micron, z1—10 micron, z2—600 nm and z3—25 micron.

Example 5

Implanting the In-Vivo MEA

Figure 13:
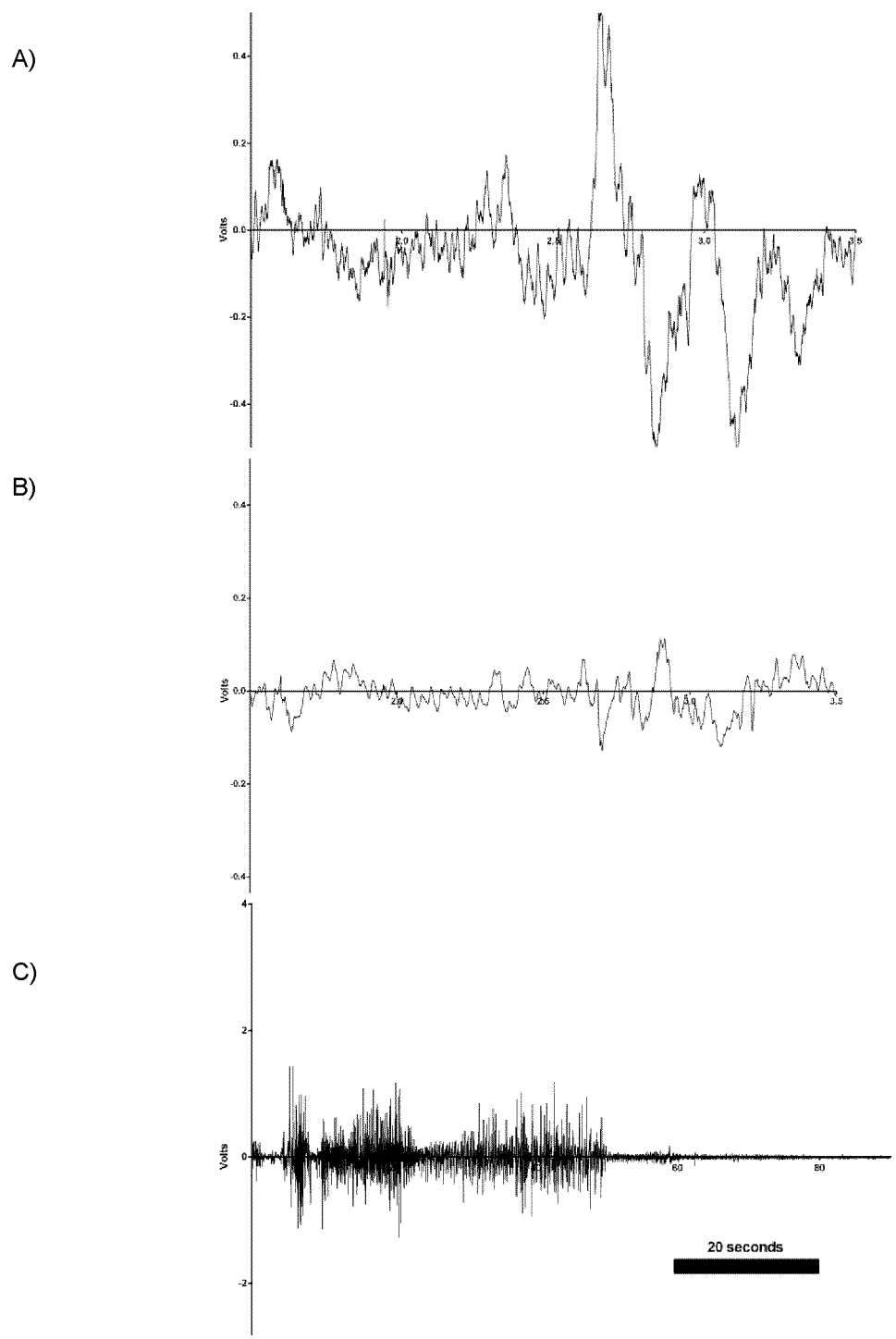

The in-vivo MEA flex PCB were surgically implanted on the sensory and motor cortex of rat brains (Sprague Dawley from Charles River Canada, n=4) for more than 8 weeks. The in vivo MEA flex PCB was held in place by a dental surgical acrylic and the scalp was held in place after implantation by the same acrylic. During which time, brain activity, including ictal phases, were successfully recorded during more than 15 different experiments (100% success rate). Ictal phases were experimentally induced by kindling In addition, the electrophysiological data collected in-vivo from the rat brains was transferred wirelessly to a computer to further the analysis of the electrophysiological activity. The data was also recorded locally onto a removable storage device, allowing for data to be backed up, and also available for later transfer. Ensuring fidelity of both recorded and transmitted data was important. The wireless data was also transmitted using compression techniques to allow live viewing of the In FIG. 13 the x-axis is time in seconds and the y-axis is in volts. FIG. 13A shows an example of baseline activity obtained from a live animal brain using a known MEA that did not have any electrical-insulating coating 108 and that had much larger dimensions than the in-vivo 3D-MEA. FIG. 13B shows an example of baseline activity obtained from a live animal brain using the in-vivo 3D-MEA. The decreased noise level from the signal obtained by the in-vivo 3D-MEA is apparent when comparing the two examples. FIG. 13C shows an example of electrical communication data obtained from a live rat brain that underwent an experimentally induced ictal phase (seizure), which was followed by a post-ictal period. The ictal phase is associated with an increased electrical activity, as evidenced by at least a ten-fold increase in detected voltage (FIG. 13B shows increments of 0.2 V on the Y axis and FIG. 13C show increments of 2 V).

Without being bound by any particular theory, the 3D micro-electrodes and 3D-MEAs described herein can be used to record activity from electrically excitable cells (Central Nervous System and Peripheral Nervous System, heart, muscle and others) and stimulate these cells using electrical stimulation. By establishing two-way electrical communication (both recording and stimulation), a feedback loop system can be established.

We claim:

1. A method of fabricating a three dimensional (3D) micro-electrode array (3D-MEA), the method comprising steps of:
    (a) forming two or more electrically conducting pads upon a substrate;
    (b) wire bonding a wire upon one of the two or more electrically conducting pads to form an elongate portion of a 3D micro-electrode;
    (c) selecting a height of the 3D micro-electrode, and cutting the wire according to the height, thereby forming a tip of the 3D micro-electrode distal to the substrate; and
    (d) coating the 3D micro-electrode with an electrical-insulating layer without coating the tip.

2. The method of claim 1, further comprising selecting a diameter of the elongate portion of the 3D micro-electrode.

3. The method of claim 2, wherein the step of selecting the diameter of the elongate portion of the 3D micro-electrode results in a first diameter of a first elongate portion of a first 3D micro-electrode upon a first pad and a second diameter of a second elongate portion of a second 3D micro-electrode upon a second pad, and wherein the two or more electrically conducting pads comprise the first pad and the second pad.

4. The method of claim 3, wherein the first diameter and the second diameter are substantially the same.

5. The method of claim 3, wherein the first diameter and the second diameter are substantially different.

6. The method of claim 1, wherein the step of selecting the height of the 3D micro-electrode results in a first height of a first 3D micro-electrode upon a first pad and a second height of a second 3D micro-electrode upon a second pad, and wherein the two or more electrically conducting pads comprise the first pad and the second pad.

7. The method of claim 6, wherein the first height and the second height are substantially the same.

8. The method of claim 6, wherein the first height and the second height are different.

9. The method of claim 1, wherein the one or more electrically conducting pads are defined between one more layers of electrical-insulating material.

* * * * *